United States Patent [19]

White

[11] 4,380,651

[45] Apr. 19, 1983

[54] PROCESS FOR PREPARING 6'-METHYLSPECTINOMYCIN AND ANALOGS THEREOF

[75] Inventor: David R. White, Kalamazoo, Mich.

[73] Assignee: The Upjohn Company, Kalamazoo, Mich.

[21] Appl. No.: 285,164

[22] Filed: Jul. 20, 1981

[51] Int. Cl.$^3$ .................. C07D 319/20; C07D 327/06
[52] U.S. Cl. ...................................... 549/361; 549/16
[58] Field of Search ................ 549/16, 361; 260/340.3

[56] References Cited

U.S. PATENT DOCUMENTS 3,981,887 9/1976 Gante et al. ........................... 549/16
4,282,152 8/1981 White ................................ 260/340.3

FOREIGN PATENT DOCUMENTS 734469 5/1966 Canada .

Primary Examiner—Ethel G. Love
Attorney, Agent, or Firm—Sidney B. Williams, Jr.

[57] ABSTRACT

A method for the preparation of 6'-methylspectinomycin and analogs thereof. Additionally provides novel intermediates utilized in said method.

4 Claims, No Drawings

PROCESS FOR PREPARING 6'-METHYLSPECTINOMYCIN AND ANALOGS THEREOF

FIELD OF THE INVENTION

The invention concerns a method for the synthesis of 6'-methyl spectinomycin and analogs thereof including intermediates utilized in the method.

DESCRIPTION OF THE PRIOR ART

Spectinomycin A is a known antibiotic and was first prepared by a microbiological process. See Bergy et al., U.S. Pat. No. 3,234,092.

Some analogs of spectinomycin are described by Rosenbrook Jr. et al., in J. Antibiotics, 28, pp. 953 and 960 (1975) and J. Antibiotics, 31, p. 451 (1978). In addition, Carney et al. describe chlorodeoxy derivatives of spectinomycin in J. Antibiotics, 30, 960 (1977). Further, 9-epi-4(R)-dihydrospectinomycin is reported by Foley et al., in J. Org. Chem., 43, 22 pp. 4355–4359 (2978). However, biological activity is not reported for any of the spectinomycin analogs and derivatives disclosed in the above-cited references.

Lemieux, Can. J. Chem., 51, p. 53 (2973) teaches a preferential reaction at the 5-hydroxyl of 2-deoxystreptamine (1) with tri-O-acetyl-2-deoxy-2-nitroso-α-D-glycopyranosyl chloride (2) to give a α-pseudodisaccharide wherein CBz is carbobenzyloxy. Mallams et al., J. Chem. Soc. Perkin I, p. 1118 (2976), extend the Lemieux reaction to synthesize di- and tri-saccharides.

Removal of oximes is taught by Lemieux et al., Can. J. Chem. 51, p. 19 (1973) and Mallams et al., J. Chem. Soc. Perkin I, p. 1097 (1976).

Hannessian et al., (1979), describe a chemical synthesis of spectinomycin.

White et al., Tetrahedron Letters, July, 1979, disclose a chemical synthesis of spectinomycin and analogs thereof. The same synthesis is disclosed in Ser. No. 150,530, filed May 26, 1980, now U.S. Pat. No. 4,351,771, which is a continuation of Ser. No. 020,172, filed Mar. 3, 1979, now abandoned.

SUMMARY OF THE INVENTION

An enoneacylate is converted to 6'-methylspectinomycin and analogs thereof. The sequence employs several versatile intermediates. The invention involves modification at C-6' using an enoneacylate.

DETAILED DESCRIPTION OF THE INVENTION

More specifically, this invention relates to a process for preparing compounds of Formula I which involves utilizing an enoneacylate VI as the starting material. The formulae referred to are set forth in Chart A. The process can be represented and illustrated in the reaction sequence of Scheme I, wherein R is hydrogen or lower alkyl, $R_1$ through $R_9$ are selected from the group consisting of hydrogen, lower alkyl, lower alkenyl, and lower alkynyl; $R'_2$, $R'_3$, $R'_6$ and $R'_7$ are selected from the group consisting of lower alkyl, lower alkenyl, lower alkynyl, and a blocking group selected from the group consisting of aralkoxycarbonyl, halogenated alkoxycarbonyl and alkoxycarbonyl; with the proviso that one of $R_2$ and $R_3$ is always hydrogen and one of $R_6$ and $R_7$ is always hydrogen, and the further proviso that one of $R'_2$ and $R'_3$ is always a blocking group and one of $R'_6$ and $R'_7$ is always a blocking group; and $R_{10}$ is acyl; A is selected from the group consisting of oxygen and sulfur, and B and $B_1$ are the same or different and are selected from the group consisting of hydrogen, hydroxy, alkoxy, o-lower alkenyl, thio, thio-lower alkyl and thio-lower alkenyl.

The numbering of carbons shown in compound I will be used in discussions thereof throughout the specification.

The compounds prepared by the process of this invention include the hydrate forms of compounds of Formula I. These compounds are hydrated at the 3' position and have the Formula I';

wherein A, B, $B_1$, and R through $R_{10}$ are the same as defined above. Also included are pharmaceutically acceptable salts of the compounds of formula I.

"Lower alkyl" means methyl, ethyl, propyl, butyl, pentyl, hexyl, heptyl, octyl, and the isomeric forms thereof.

"Lower alkenyl" means ethylidene, propylidene, butylidene, pentylidene, hexylidene, heptylidene, octylidene, and the isomeric forms thereof.

"Lower alkynyl" means ethenyl, propynyl, butynyl, pentynyl, hexynyl, heptynyl, octynyl and the isomeric forms thereof.

"Acyl" means formyl, acetyl, propionyl, butyryl and pentoinyl.

"Halogenated alkoxycarbonyl" means mono-, di-, tri-halomethoxycarbonyl; mono-, di-, tri-haloethoxycarbonyl; mono-, tri-halopropoxycarbonyl; mono-, di-, tri-halobutoxycarbonyl, mono-, di-, tri-halopentoxycarbonyl and isomeric forms thereof.

"Halo" means fluoro, chloro, bromo and iodo.

"Aralkoxycarbonyl" means benzyloxycarbonyl, phenethoxycarbonyl, phenpropoxycarbonyl, diphenyloctoxycarbonyl and isomeric forms thereof and fluoroenylmethoxy carbonyl.

"Alkoxycarbonyl" means isopropyloxy carbonyl, tertiary-butyloxy carbonyl, and tertiary-pentyloxycarbonyl.

It is meant that as used in this description and in the appended claims that when more than one hydroxy or alkoxy is present on the sugar moiety herein they may be the same or different.

Thus, the invention process realizes the importance of the stereochemistry at the glycosidic bond, i.e., 1' position of compounds of Formula I.

The term "α-anomer" means a 1' substituent below the plane of the ring system and the term "β-anomer" means that anomers having the C-1' configuration corresponding to spectinomycin.

Compounds prepared by the process of this invention which exhibit desirable biological activity are β-anomers of compound I. This glycosidic configuration is found in spectinomycin shown in Chart A. Therefore, adequate selectivity at the 1' position is desirable to obtain biologically active analogs of spectinomycin.

The process of this invention is exemplified in Scheme A.

In Step 1, enoneacylate IV is reacted with dimethylformamide dimethyl acetal in a solvent to yield the enamine III. The temperature range of the reaction is generally 25° C. to reflux, preferably 40° C. to 80° C. Time of the reaction may range from 1 hr. to 48 hrs., preferably 2 hrs. to 10 hrs. Dimethylformamide dimethylacetal is used in excess. The preferred reaction time and solvent is 7 hrs. and dimethylformamide. Other acetals of dimethylformamide such as di-t-butyl can also be used.

The starting enonacylate and methods for preparing it are described in U.S. application Ser. No. 150,530 filed May 16, 1980.

The enamine can be isolated from the mixture by conventional procedures such as crystallization, extraction, chromatography and combinations thereof.

Step 2 involves reduction of enamine III to give a mixture containing I. The reduction is carried out by hydrogenation in the presence of a solvent and a catalyst at a temperature of between about 100° and 100° and a reduction time of about 1 about 40 hrs. Catalysts that can be used include palladium and barium sulfate, palladium hydroxide, and palladium/barium sulfate. The preferred catalyst is palladium/barium sulfate. Suitable solvents include methanol, 2-propanol and ethyl acetate.

In Step 3, the crude mixture of I obtained in Step 2 is reacted with a blocking group to yield the protected compound of formula II. This step is necessary because the 6'-methylspectinomycin compounds cannot be readily purified directly. The reaction is conducted in the presence of a solvent at a temperature of about −10° to about 80° for a time of about 2 hrs. to about 60 hrs. Solvents that can be utilized include acetonitrile, dioxane and tetrahydrofuran. The preferred solvent is acetonitrile.

The compound of Formula II' is removed from the reaction mixture by conventional procedures such as filtration, extraction, chromatography and combinations thereof. The preferred method of recovery is by chromatography.

Step 4 involves deprotection of II to yield I. The particular conditions of deprotection depends upon the particular groups, i.e. group $R'_2$ or $R'_3$ and $R'_6$ or $R'_7$ that block the amine on the actinamine ring. Where that group is benzyloxy carbonyl or aralkoxy carbonyl the deprotection can be conducted under from −10 psi to +200 psi of hydrogen over a conventional catalyst such as palladium black, palladium on carbon, palladium on barium sulfate, or palladium on barium carbonate, while suspended in a solvent, for example, isopropanol, absolute ethanol, ethyl acetate, toluene or tetrahydrofuran.

Alternatively, deblocking of compounds wherein $R'_2$, $R'_3$ and $R'_6$ or $R'_7$ are alkoxycarbonyl or aryloxycarbonyl can be conducted in the presence of an acid in solvent such as nitromethane and methylene chloride. Deprotection is effected by reacting II with hydrogen chloride at a temperature of between about −20° and about 50° for a period of about 5 min. and about 500 min. Preferred reaction temperatures and times are between about −100° C. and about +10° C. and about ½-2 hrs., respectively. When $R'_2$ or $R'_3$ and $R'_6$ or $R'_7$ are haloalkoxycarbonyl, the deblocking is preferably conducted in the presence of zinc.

Any method within the skill in the art may be used for isolation of an analog or asteric mixture of a compound having Formula I and methods disclosed herein are not meant to be limiting. If isolation is conducted under anhydrous conditions, compounds having a carbonyl group at the 3' position (Formula I) are obtained. If conducted under aqueous conditions, compounds hydrated at the 3' position are obtained. One such method includes evaporation of the excess solvent and formation of a crystalline salt of the compound. These salts may be formed using a solution of an acid such as toluene sulfonic acid, hydrochloric acid, hydrobromic acid, hydroiodic acid or other acids in a solvent such as water, methanol, ethanol, isopropanol, ether, 1,2-dimethoxyethane or p-dioxane. The salt is isolated by filtration and direct crystallization or by evaporation of the solvent followed by subsequent recrystallization from a suitable solvent.

Alternatively, the crude analogs may be purified by adsorption on a column of a weakly acidic ion exchange resin such as Amberlite IRC-50 or CG-50 followed by elution with a solvent such as water, methanol, ethanol, ether, tetrahydrofuran, 1,2-dimethoxy, 1,2-dimethyloxy ethane or p-dioxane containing hydrochloric acid, hydrobromic acid, hydroiodic acid and sulfuric acid.

Each step of the above process can be conducted on asteric mixtures of various anomers or on the desired β anomer itself obtained by resolution or separation at any stage in the process. The remaining steps may be conducted on β-intermediates resulting in the desired biologically active isomers.

Separation of the anomers from asteric mixtures can be accomplished with modifications obvious to those skilled in the art utilizing conventional methods of resolution. For example, compound IV may be separated so as to obtain a desired β component by chromatography on a silica gel column eluted with a mixture of methanol in chloroform in the ration of 1:99 to 2:98.

Acid salts can be made by neutralizing compounds of Formula I with the appropriate acid to below about pH 7.0 and advantageously to about pH 2 to pH 6. Suitable acids for this purpose include hydrochloric, sulfuric, phosphoric, sulfamic, hydrobromic and the like. Acid and base salts of the compounds can be used for the same biological purposes as the parent compound.

The compounds of Formula I inhibit the growth of microorganisms in various environments. For example, Formula I compounds having the β configuration are active against *Escherichia coli* and can be used to reduce, arrest, and eradicate slime production in papermill systems caused by its antibacterial action against this microorganism. These β anomers also can be used to prolong the life of cultures of *Trichomonas foetus, Trichomonas hominis,* and *Trichomonas vaginalis* by freeing them of *Escherichia coli* contamination. Still further, β anomers are active against *Bacillus subtilis* so it can be used to minimize or prevent odor in fish or fish crates caused by this organism. Also, the anomers can be used to swab laboratory benches and equipment in a mycological laboratory. β-anomers are also effective against *Klebsiella pneumoniae.*

The compounds of Formula I are also effective for treating bacterial infections, such as gonorrhea in mammals, including humans.

The compositions of the present invention are presented for administration to humans and animals in unit dosage forms, such as tablets, capsules, pills, powders, granules, sterile parenteral solutions or suspensions, eye drops and water-in-oil emulsions containing suitable quantities of the compound of Formula I.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspension can be prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The term "unit dosage form" as used in the specification refers to physically discrete units suitable as unitary dosages for human subjects and animals, each unit containing a predetermined quantity of active material calculated to produce the desired therapeutic effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention. Examples of suitable unit dosage forms in accord with this invention are ampoules, vials, aerosols with metered discharges, segregated multiples of any of the foregoing, and other forms as herein described.

An effective quantity of the compound is employed in treatment. The dosage of the compound for treatment depends on many factors that are well known to those skilled in the art. They include for example, the route of administration and the potency of the particular compound. A dosage schedule for humans of from about 2 to about 4000 mg of compound in a single dose, administered parenterally or in the compositions of this invention, are effective for treating bacterial infections. More specifically, the single dose is from 5 mg to about 200 mg of compound.

The following described preparations of analogs of spectinomycin and intermediates useful in the preparation thereof are indicative of the scope of this invention and are not to be construed as limitative. Those skilled in the art will promptly recognize variations from the procedures both in the analogs and analog precursors within the novel compounds described as well as reaction conditions and techniques of the invention process.

For example, for each of the Preparations and Examples in the following descriptions, corresponding stereoisomers for each named compound is contemplated to be within the scope of the invention.

PREPARATION 1

Enamine of N,N-dicarbobenzyloxy-2'-O-acetyl-4,5'-didehydrospectinomycin

A solution of N,N-dicarbobenzyloxy-2'-O-acetyl-4,5'-didehydrospectinomycin (22.00 g., 34.4 mmole) and dimethylformamide dimethylacetal (100 ml) in dimethylformamide (100 ml) is stirred for 7 hours at 50°–55° C. with drierite protection. The brown solution is concentrated under vacuum and the residue is chromatographed on silica gel (250 g) which has been wet packed in a 2 liter sintered glass funnel. The mixture is eluted with 5% acetonitrile in chloroform (2 liters), 7% (3 liters), 33% (3 liters), 50% (6 liters) over a period of 1½ hours. Half liter fractions are taken. The fractions are evaluated by TLC (1/1 acetonitrile in chloroform) and combined to give 19.78 g of pure enamine and 3.30 g of enamine containing some dimethylformamide. The latter fraction was rechromatographed as above (but using 60 g of silica gel) to give 2.75 g of pure enamine. Total yield is 22.53 g (94% yield).

CD(CH$_3$OH)[$\theta$]$_{311}$nm—10,400±1,200, [$\theta$]$_{285}$—2,5000±1,200, [$\theta$]$_{246}$—1,200±1,200.

IR(mull): 3380, 1750, 1695, 1675sh, 1600, 1555, 1500, 1385, 1350, 1280, 1240, 1195, 1185, 1145, 1110, 1085, 1065, 1025, 1000, 960, 770, 740, 645 cm$^{-1}$.

PMR (CDCl$_3$): 2.13, (3H, s), 2.82 (3H, s), 2.89 (6H, br.s), 2.91 (3H, s), 5.10 (4H, br.s), 5.16 (1H, s), 5.97 (1H, s), 7.30$\delta$ (10H, s).

CMR (CD$_3$COCD$_3$): 20.9, 31.2, 31.5, 30–44 br, 36.3, 59.6, 66.2, 67.3, 74.6, 75.4, 88.7, 94.9, 95.0, 95.1, 95.5, 128.3, 129.1, 137.9, 138.0, 150.3, 157.2, 157.7, 163.3, 169.8, 171.2, 180.3 ppm.

Mass spectrum, m/c (diTMS): 839 (M+), 824, 797, 730, 688. Peak matched calcd: 839.3480; Found: 839.3466.

Utilizing a procedure similar to Preparation 1, but substituting the appropriately-substituted actinamine and sugar reactants, there is obtained the enamine of Tables I and II.

TABLE I

| B | B$_1$ | R$_{10}$ |
|---|---|---|
| HO— | HO— | O‖CH$_3$C— |
| CH$_3$O— | HO— | O‖CH$_3$C— |
| C$_2$H$_5$O— | HO— | O‖CH$_3$C— |
| HS— | HO— | O‖CH$_3$C— |
| CH$_3$S— | HO— | O‖CH$_3$C— |
| C$_2$H$_5$S— | HO— | O‖CH$_3$C— |
| H— | HO— | O‖CH$_3$C— |
| HO— | H— | O‖CH$_3$C— |
| HO— | CH$_3$O— | O‖CH$_3$C— |

TABLE I-continued

[Structure: cyclohexane ring with CBz-N(CH3)- at top left, B substituent, C=O, connected to pyranone ring with OR10, linked to CH=CH-N(CH3)2; B1 and N(CH3)-CBz substituents on ring]

| B | B₁ | R₁₀ |
|---|---|---|
| HO— | C₂H₅O— | CH₃C(=O)— |
| HO— | HS— | CH₃C(=O)— |
| HO— | CH₃S— | CH₃C(=O)— |
| HO— | C₂H₅S— | CH₃CH₂C(=O)— |
| HO— | HO— | CH₂CH₂C(=O)— |
| HO— | HO— | CH₃(CH₂)₂C(=O)— |
| HO— | HO— | CH₃(CH₂)₂C(=O)— |
| HO— | HO— | CH₃(CH₂)₃C(=O)— |
| HO— | HO— | isopropionyl |
| HO— | HO— | sec-butyryl |
| HO— | HO— | t-butyryl |

TABLE II

[Structure similar to Table I but with S (sulfur) in the pyranone ring position instead of O]

| B | B₁ | R₁₀ |
|---|---|---|
| HO— | HO— | CH₃C(=O)— |
| CH₃O— | HO— | CH₃C(=O)— |
| C₂H₅O— | HO— | CH₃C(=O)— |
| HS— | HO— | CH₃C(=O)— |
| CH₃S— | HO— | CH₃C(=O)— |

TABLE II-continued

| B | B₁ | R₁₀ |
|---|---|---|
| C₂H₅S— | HO— | CH₃C(=O)— |
| H— | HO— | CH₃C(=O)— |
| HO— | H— | CH₃C(=O)— |
| HO— | CH₃O— | CH₃C(=O)— |
| HO— | C₂H₅— | CH₃C(=O)— |
| HO— | H₂ | CH₃C(=O)— |
| HO— | CH₃S— | CH₃C(=O)— |
| HO— | C₂H₅S— | CH₂CH₂C(=O)— |
| HO— | HO— | CH₂CH₂C(=O)— |
| HO— | HO— | CH₃(CH₂)₂C(=O)— |
| HO— | HO— | CH₃(CH₂)₂C(=O)— |
| HO— | HO— | CH₃(CH₂)₃C(=O)— |
| HO— | HO— | CH₃(CH₂)₃C(=O)— |
| HO— | HO— | isopropionyl |
| HO— | HO— | sec-butyryl |
| HO— | HO— | t-butyryl |

PREPARATION 2

N,N-di-t-butoxycarbonyl-6'-methylspectinomycin

The enamine of N,N'-dicarbobenzyloxy-6'-methylspectinomycin (0.90 g., 1.29 mmole) is dissolved in 2-propanol (90 ml) and pyridine (0.90 ml) and then 10% palladium on barium sulfate (ionic palladium, brown catalyst) (0.90 g) is added. The mixture is stirred well under 1 atm H₂ for 5¾ hours. The solids are filtered and the filtrate concentrated finally under high vacuum.

The residue is dissolved in acetonitrile (18 ml) and t-butanol (15 ml) and di-t-butyl-di-carbonate (0.90 g) is added. After stirring at room temperature for 16 hours, the solution is concentrated and chromatographed on silica gel (150 ml) using 5/95 methanol in chloroform. This gross purification gives a mixture having approximately the same $R_f$ (in 1/9 methanol/chloroform) as N,N'-di-t-butyloxycarbonylspectinomycin. The mixture is rechromatographed on silica gel (6 g) using ¼ acetonitrile/chloroform to yield 16 mg of N,N'-di-t-butoxycarbonyl-6-'methylspectinomycin.

CMR (CD$_3$COCD$_3$): 97.8, 92.7, 79.7, 75.6, 75.2, 74.7, 73.2, 66.5, 66.0, 60.6, 60.5, 57.5, 57.1, 44.0, 31.5, 28.7, 9.8 ppm.

Using a procedure similar to that of Preparation 2 but substituting the appropriately substituted precursor enamine from Tables I and II, there is obtained the protected spectinomycin analogs of Tables III and IV.

TABLE III

| B | B$_1$ | R$_{10}$ |
|---|---|---|
| HO— | HO— | CH$_3$C(=O)— |
| CH$_3$O— | HO— | CH$_3$C(=O)— |
| C$_2$H$_5$O— | HO— | CH$_3$C(=O)— |
| HS— | HO— | CH$_3$C(=O)— |
| CH$_3$S— | HO— | CH$_3$C(=O)— |
| C$_2$H$_5$S— | HO— | CH$_3$C(=O)— |
| H— | HO— | CH$_3$C(=O)— |
| HO— | H— | CH$_3$C(=O)— |
| HO— | CH$_3$O— | CH$_3$C(=O)— |
| HO— | C$_2$H$_5$O— | CH$_3$C(=O)— |
| HO— | HS— | CH$_3$C(=O)— |
| HO— | CH$_3$S— | CH$_3$C(=O)— |
| HO— | C$_2$H$_5$S— | CH$_3$CH$_2$C(=O)— |
| HO— | HO— | CH$_2$CH$_2$C(=O)— |
| HO— | HO— | CH$_3$(CH$_2$)$_2$C(=O)— |
| HO— | HO— | CH$_3$(CH$_2$)$_2$C(=O)— |
| HO— | HO— | CH$_3$(CH$_2$)$_2$C(=O)— |
| HO— | HO— | CH$_3$(CH$_2$)$_3$C(=O)— |
| HO— | HO— | isopropionyl |
| HO— | HO— | sec-butyryl |
| HO— | HO— | t-butyryl |

TABLE IV

| B | B$_1$ | R$_{10}$ |
|---|---|---|
| HO— | HO— | CH$_3$C(=O)— |
| CH$_3$O— | HO— | CH$_3$C(=O)— |
| C$_2$H$_5$O— | HO— | CH$_3$C(=O)— |
| HS— | HO— | CH$_3$C(=O)— |
| CH$_3$S— | HO— | CH$_3$C(=O)— |
| C$_2$H$_5$S— | HO— | CH$_3$C(=O)— |
| H— | HO— | CH$_3$C(=O)— |

TABLE IV-continued

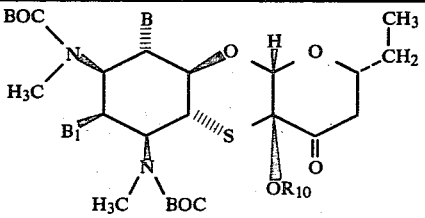

| B | B₁ | R₁₀ |
|---|---|---|
| HO— | H— | $CH_3\overset{O}{\underset{\|}{C}}-$ |
| HO— | CH₃O— | $CH_3\overset{O}{\underset{\|}{C}}-$ |
| HO— | C₂H₅— | $CH_3\overset{O}{\underset{\|}{C}}-$ |
| HO— | H₂ | $CH_3\overset{O}{\underset{\|}{C}}-$ |
| HO— | CH₃S— | $CH_3\overset{O}{\underset{\|}{C}}-$ |
| HO— | C₂H₅S— | $CH_3CH_2\overset{O}{\underset{\|}{C}}-$ |
| HO— | HO— | $CH_3CH_2\overset{O}{\underset{\|}{C}}-$ |
| HO— | HO— | $CH_3(CH_2)_2\overset{O}{\underset{\|}{C}}-$ |
| HO— | HO— | $CH_3(CH_2)_2\overset{O}{\underset{\|}{C}}-$ |
| HO— | HO— | $CH_2(CH_2)_3\overset{O}{\underset{\|}{C}}-$ |
| HO— | HO— | $CH_3(CH_2)_3\overset{O}{\underset{\|}{C}}-$ |
| HO— | HO— | isopropionyl |
| HO— | HO— | sec-butyryl |
| HO— | HO— | t-butyryl |

EXAMPLE 1

6'-Methylspectinomycin

N,N'-di-t-butyloxycarbonyl-6'-methylspectinomycin (16 mg., 0.029 mmole) is dissolved in methylene chloride (2.0 ml) and cooled to 0° C. The solution is saturated with dry HCL gas; after 1 hour the mixture is concentrated to give 6'-methylspectinomycin-dihydrochloride dihydrate.

CMR (CD₂O, CH₃CN as IS=O): 92.8, 90.7, 72.2, 68.9, 65.1, 60.7, 58.7, 57.8, 38.1, 30.0, 29.4, 26.0, 7.6 ppm.

Mass spectrum (penta TMS): 706 (M+), 691, 603, 567, 547, 513, 217, 145.

Exact mass calcd. for $C_{30}H_{66}N_2O_7Si_5$ is 706.3716. Found: 706.3738.

Using a procedure similar to that of Example 1, but substituting the appropriately substituted derivative, there is obtained the deprotected spectinomycin analogs of Tables V and VI.

TABLE V

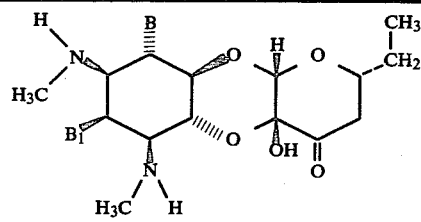

| B | B₁ |
|---|---|
| HO— | HO— |
| CH₃O— | HO— |
| C₂H₅O— | HO— |
| HS— | HO— |
| CH₃S— | HO— |
| C₂H₅S— | HO— |
| H— | HO— |
| HO— | H— |
| HO— | CH₃O— |
| HO— | C₂H₅O— |
| HO— | HS— |
| HO— | CH₃S— |
| HO— | C₂H₅S— |
| HO— | HO— |
| HO— | HO— |
| HO— | HO— |
| HO— | HO— |
| HO— | HO— |
| HO— | HO— |
| HO— | HO— |

TABLE VI

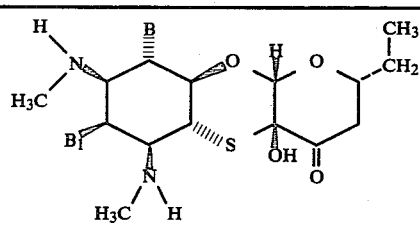

| B | B₁ |
|---|---|
| HO— | HO— |
| C₃O— | HO— |
| C₂H₅O— | HO— |
| HS— | HO— |
| CH₃S— | HO— |
| C₂H₅S— | HO— |
| H— | HO— |
| HO— | H— |
| HO— | CH₃O— |
| HO— | C₂H₅O— |
| HO— | HS— |
| HO— | CH₃S— |
| HO— | C₂H₅S— |
| HO— | HO— |
| HO— | HO— |
| HO— | HO— |
| HO— | HO— |
| HO— | HO— |
| HO— | HO— |
| HO— | HO— |

CHART A
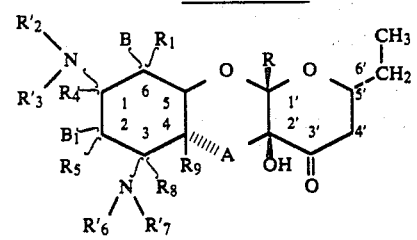
I
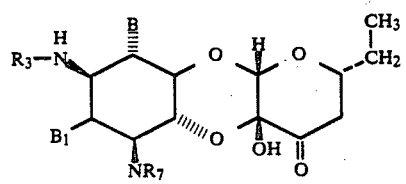
Ia
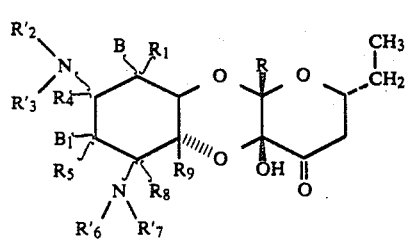
II
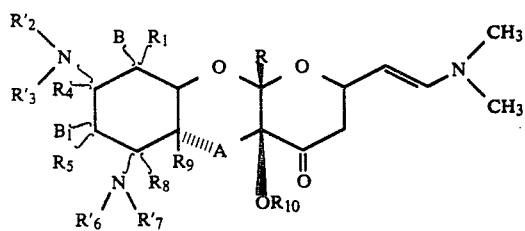
III
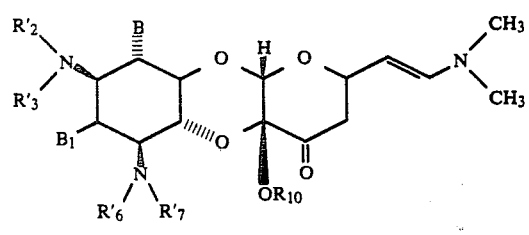
IIIa
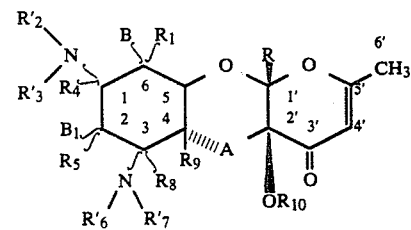
IV
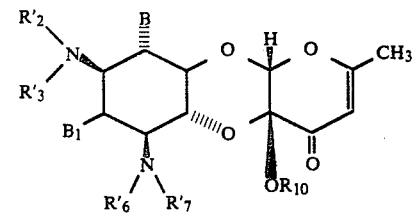
IVa
SCHEME A
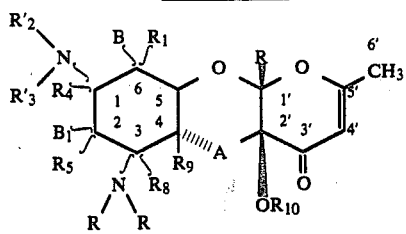
IV
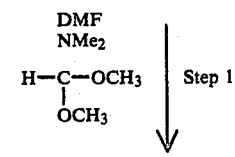
Step 1
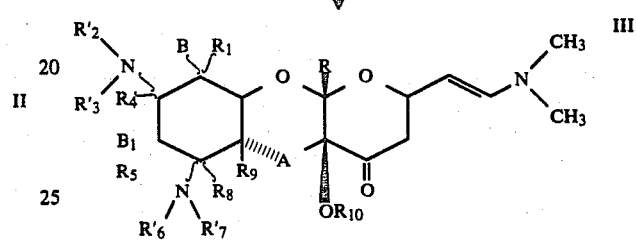
III
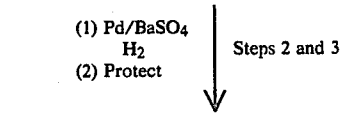
Steps 2 and 3
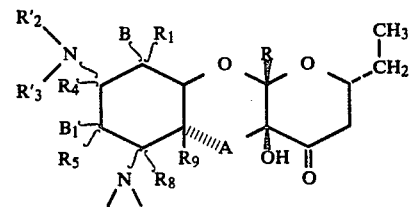
II
Step 4
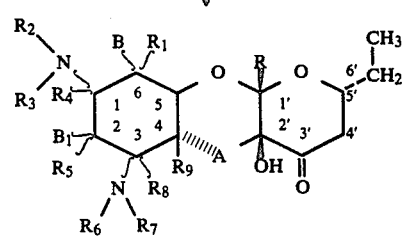
I
I claim:
1. A process for preparing a compound having the formula
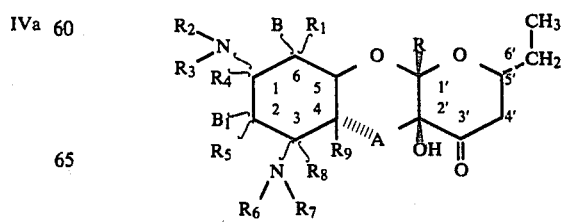

which comprises reducing a compound having the formula

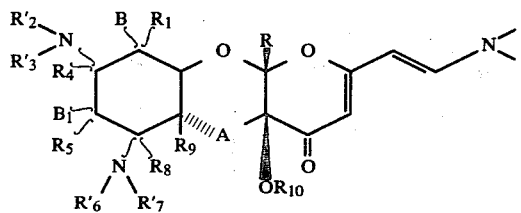

with hydrogen in the presence of a catalyst selected from the group consisting of palladium, barium sulfate, palladium hydroxide, and palladium/barium sulfate; wherein R is hydrogen or alkyl and $R_1$ through $R_9$ are selected from the group consisting of hydrogen, lower alkyl, lower alkenyl and lower alkynyl with the proviso that one of $R_2$ and $R_3$ is always hydrogen and one of $R_6$ and $R_7$ is always hydrogen, and B and $B_1$ are the same or different and are selected from the group consisting of hydrogen, hydroxy, alkoxy, o-lower alkenyl, thio, thio-lower alkyl and thio-lower alkenyl; and A is selected from the group consisting of oxygen and sulfur; $R'_2$, $R'_3$, $R'_6$ and $R'_7$ are selected from the group consisting of lower alkyl, lower alkenyl, lower alkynyl, and a blocking group selected from the group consisting of aralkoxycarbonyl, halogenated-alkoxycarbonyl, with the proviso that one of $R'_2$ and $R'_3$ is always a blocking group and one of $R'_6$ and $R'_7$ is always a blocking group; and $R_{10}$ is acyl.

2. A process according to claim 1 wherein the product prepared has the formula

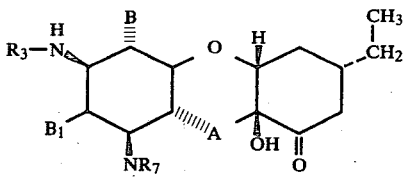

wherein $R_3$ and $R_7$ are lower alkyl and B and $B_1$ are selected from the group consisting of hydroxy or lower alkoxy.

3. A process according to claim 2 wherein the compound prepared is 6'-methylspectinomycin.

4. A process according to claim 1, 2 or 3 wherein the catalyst used is palladium/barium sulfate.

* * * * *